(12) United States Patent
Zapp et al.

(10) Patent No.: US 10,080,376 B2
(45) Date of Patent: *Sep. 25, 2018

(54) METHOD FOR ENHANCING POSTPROCESSING CONTENT OF BENEFICIAL COMPOUNDS IN BEVERAGES NATURALLY CONTAINING SAME

(71) Applicants: ONCOLOGY SCIENCES CORPORATION, Austin, TX (US); The Regents of the University of Colorado, a body corporate, Denver, CO (US)

(72) Inventors: Loretta Zapp, Boulder, CO (US); Thomas J. Slaga, Austin, TX (US); Jifu Zhao, Olympia, WA (US); Mark Lange, Rougemont, NC (US)

(73) Assignees: ONCOLOGY SCIENCES CORPORATION, Austin, TX (US); THE REGENTS OF THE UNIVERSITY OF COLORADO, A BODY CORPORATE, Denver, CO (US)

( * ) Notice: Subject to any disclaimer, the term of this patent is extended or adjusted under 35 U.S.C. 154(b) by 292 days.

This patent is subject to a terminal disclaimer.

(21) Appl. No.: 14/486,700

(22) Filed: Sep. 15, 2014

(65) Prior Publication Data
US 2015/0004294 A1    Jan. 1, 2015

Related U.S. Application Data

(63) Continuation of application No. 13/741,663, filed on Jan. 15, 2013, now abandoned, which is a continuation of application No. 12/749,163, filed on Mar. 29, 2010, now Pat. No. 8,357,419, which is a continuation of application No. 10/962,758, filed on Oct. 12, 2004, now Pat. No. 7,713,566, which is a continuation-in-part of application No. 10/493,780, filed as application No. PCT/US02/35053 on Oct. 31, 2002, now abandoned, which is a continuation-in-part of application No. 10/001,928, filed on Oct. 31, 2001, now Pat. No. 6,723,368, which is a continuation-in-part of application No. 09/843,543, filed on Apr. 25, 2001, now abandoned, which is a continuation-in-part of application No. 09/481,279, filed on Jan. 11, 2000, now Pat. No. 6,669,979, which is a continuation-in-part of application No. 09/468,560, filed on Dec. 21, 1999, now abandoned.

(51) Int. Cl.
| | | |
|---|---|---|
| A23F 5/10 | (2006.01) | |
| A23F 5/00 | (2006.01) | |
| A23F 5/24 | (2006.01) | |
| A23F 5/02 | (2006.01) | |
| A23F 5/04 | (2006.01) | |
| A23F 5/14 | (2006.01) | |
| A23F 5/26 | (2006.01) | |
| A61K 36/74 | (2006.01) | |

(52) U.S. Cl.
CPC ............... *A23F 5/10* (2013.01); *A23F 5/00* (2013.01); *A23F 5/02* (2013.01); *A23F 5/04* (2013.01); *A23F 5/14* (2013.01); *A23F 5/24* (2013.01); *A23F 5/267* (2013.01); *A61K 36/74* (2013.01)

(58) Field of Classification Search
CPC ...... A23F 5/00; A23F 5/02; A23F 5/04; A23F 5/10; A23F 5/14; A23F 5/24; A23F 5/267; A61K 36/74
See application file for complete search history.

(56) References Cited

U.S. PATENT DOCUMENTS

| | | |
|---|---|---|
| 312,516 A | 2/1885 | Schilling |
| 3,114,641 A | 12/1963 | Sperti et al. |
| 3,379,049 A | 4/1968 | Golay |
| 3,657,424 A | 4/1972 | Atkins et al. |
| 3,671,263 A | 6/1972 | Patel et al. |
| 3,799,049 A | 3/1974 | Smith, Jr. |
| 4,053,652 A | 10/1977 | Mahlmann |
| 4,156,031 A | 5/1979 | Hamell et al. |
| 4,279,937 A | 7/1981 | Strobel et al. |
| 4,325,975 A | 4/1982 | Lindon et al. |
| 4,328,255 A | 5/1982 | Roselius et al. |

(Continued)

FOREIGN PATENT DOCUMENTS

| | | |
|---|---|---|
| EP | 0075114 | 3/1983 |
| EP | 1370118 | 12/2003 |

(Continued)

OTHER PUBLICATIONS

U.S. Appl. No. 09/468,560 dated Sep. 12, 2000, Office Action in the U.S. Patent and Trademark Office.
U.S. Appl. No. 09/481,279 dated Feb. 12, 2001, Office Action in the U.S. Patent and Trademark Office.
U.S. Appl. No. 09/481,279 dated Jul. 1, 2003, Notice of Allowance in the U.S. Patent and Trademark Office.
U.S. Appl. No. 09/843,543 dated Apr. 26, 2002, Office Action in the U.S. Patent and Trademark Office.
U.S. Appl. No. 09/993,315 dated Jul. 31, 2003, Notice of Allowance in the U.S. Patent and Trademark Office.

(Continued)

*Primary Examiner* — Anthony Weier
(74) *Attorney, Agent, or Firm* — Porzio, Bromberg & Newman P.C.

(57) ABSTRACT

A process for enhancing polyphenolics content of beverages brewed from polyphenolic containing, processed beverage substrate by pre-soaking substrate (coffee beans, for example) before roasting and then quenching the substrate after processing with the liquid in which the substrate was first "pre-soaked." Beverages produced from the treated substrate exhibit substantially increased polyphenolics content, when compared to conventionally processed beverage substrate of the same nature and processing.

13 Claims, No Drawings

(56) References Cited

U.S. PATENT DOCUMENTS

| | | | |
|---|---|---|---|
| 4,486,413 A | 12/1984 | Wiesenberger et al. | |
| 4,497,800 A | 2/1985 | Larson et al. | |
| 4,626,435 A | 12/1986 | Zimmerman | |
| 4,722,847 A | 2/1988 | Heckert | |
| 4,737,375 A | 4/1988 | Nakel et al. | |
| 4,740,380 A | 4/1988 | Melachouris et al. | |
| 4,798,732 A | 1/1989 | Osawa | |
| 4,851,221 A | 7/1989 | Pak et al. | |
| 4,857,351 A | 8/1989 | Neilson et al. | |
| 4,883,651 A * | 11/1989 | Meyer | A61K 8/97 424/47 |
| 4,904,484 A | 2/1990 | Small et al. | |
| 4,919,963 A | 4/1990 | Heckert | |
| 4,985,271 A | 1/1991 | Neilson et al. | |
| 5,045,334 A | 9/1991 | Kopsch et al. | |
| 5,232,709 A | 8/1993 | Saltman et al. | |
| 5,716,649 A | 2/1998 | Nam | |
| 5,928,646 A | 7/1999 | Nkiliza | |
| 6,045,843 A | 4/2000 | Gurol | |
| 6,086,927 A | 7/2000 | Frielich et al. | |
| 6,093,436 A | 7/2000 | Zheng et al. | |
| 6,102,213 A | 8/2000 | Gurol | |
| 6,106,874 A | 8/2000 | Liebrecht et al. | |
| 6,312,753 B1 | 11/2001 | Kealey et al. | |
| 6,458,392 B1 | 10/2002 | Okawa et al. | |
| 6,469,053 B1 * | 10/2002 | Romanczyk, Jr. | A61K 9/2068 514/456 |
| 6,495,180 B1 | 12/2002 | Gurol | |
| 6,572,915 B1 * | 6/2003 | Drunen | A23F 5/14 426/425 |
| 6,660,322 B2 * | 12/2003 | Zapp | A23F 5/14 426/431 |
| 6,669,979 B1 * | 12/2003 | Zhao | A23F 5/267 426/442 |
| 6,723,368 B1 * | 4/2004 | Zapp | A23F 5/02 426/431 |
| 7,713,566 B2 * | 5/2010 | Zapp | A23F 5/267 426/431 |
| 8,357,419 B2 * | 1/2013 | Zapp | A23F 5/267 426/431 |
| 2004/0253356 A1 | 12/2004 | Fields | |
| 2011/0039012 A1 | 2/2011 | Fields | |

FOREIGN PATENT DOCUMENTS

| | | |
|---|---|---|
| FR | 2734479 | 11/1996 |
| JP | S5716649 | 1/1982 |
| JP | S6174543 | 4/1986 |
| JP | S62111633 | 5/1987 |
| JP | S63254950 | 10/1988 |
| JP | H0239872 | 2/1990 |
| JP | 3127973 | 12/1991 |
| JP | 4145048 | 5/1992 |
| JP | H04145049 | 5/1992 |
| JP | H06206785 | 7/1994 |
| JP | H07145067 | 6/1995 |
| JP | H07155133 | 6/1995 |
| JP | H0799998 | 11/1995 |
| JP | H08151319 | 6/1996 |
| JP | H08157816 | 6/1996 |
| JP | H08301721 | 11/1996 |
| JP | H10120696 | 5/1998 |
| JP | 4145049 | 9/2008 |
| WO | WO-9966881 | 12/1999 |
| WO | WO-01/50885 | 7/2001 |
| WO | WO-01/66106 | 9/2001 |
| WO | WO-02/060462 | 8/2002 |
| WO | WO-02085397 | 10/2002 |
| WO | WO-03/37097 | 5/2003 |
| WO | WO-2004110382 | 12/2004 |

OTHER PUBLICATIONS

U.S. Appl. No. 10/001,928 dated Sep. 10, 2003, Notice of Allowance in the U.S. Patent and Trademark Office.
U.S. Appl. No. 10/458,754 dated Dec. 22, 2010, Office Action in the U.S. Patent and Trademark Office.
U.S. Appl. No. 10/458,754 dated Mar. 14, 2007, Office Action in the U.S. Patent and Trademark Office.
U.S. Appl. No. 10/458,754 dated Apr. 27, 2010, Final Office Action in the U.S. Patent and Trademark Office.
U.S. Appl. No. 10/458,754 dated Aug. 10, 2015, Final Office Action in the U.S. Patent and Trademark Office.
U.S. Appl. No. 10/458,754 dated Aug. 17, 2006, Restriction/Election Requirement in the U.S. Patent and Trademark Office.
U.S. Appl. No. 10/458,754 dated Aug. 18, 2011, Final Office Action in the U.S. Patent and Trademark Office.
U.S. Appl. No. 10/458,754 dated Sep. 22, 2014, Office Action in the U.S. Patent and Trademark Office.
U.S. Appl. No. 10/476,109 dated Dec. 28, 2004, Restriction/Election Requirement in the U.S. Patent and Trademark Office.
U.S. Appl. No. 10/493,780 dated Mar. 25, 2005, Office Action in the U.S. Patent and Trademark Office.
U.S. Appl. No. 10/827,892 dated Jan. 27, 2006, Final Office Action in the U.S. Patent and Trademark Office.
U.S. Appl. No. 10/827,892 dated Feb. 5, 2007, Final Office Action in the U.S. Patent and Trademark Office.
U.S. Appl. No. 10/827,892 dated May 2, 2005, Office Action in the U.S. Patent and Trademark Office.
U.S. Appl. No. 10/827,892 dated Aug. 22, 2006, Office Action in the U.S. Patent and Trademark Office.
U.S. Appl. No. 10/962,758 dated Nov. 13, 2008, Office Action in the U.S. Patent and Trademark Office.
U.S. Appl. No. 10/962,758 dated Nov. 28, 2007, Restriction/Election Requirement in the U.S. Patent and Trademark Office.
U.S. Appl. No. 10/962,758 dated Jul. 24, 2009, Notice of Allowance in the U.S. Patent and Trademark Office.
U.S. Appl. No. 12/749,163 dated May 9, 2012, Final Office Action in the U.S. Patent and Trademark Office.
U.S. Appl. No. 12/749,163 dated Jun. 20, 2011, Office Action in the U.S. Patent and Trademark Office.
U.S. Appl. No. 12/749,163 dated Sep. 17, 2012, Notice of Allowance in the U.S. Patent and Trademark Office.
U.S. Appl. No. 12/913,745 dated Feb. 4, 2013, Office Action in the U.S. Patent and Trademark Office.
U.S. Appl. No. 12/913,745 dated Jun. 3, 2013, Office Action in the U.S. Patent and Trademark Office.
U.S. Appl. No. 12/913,745 dated Jun. 9, 2011, Restriction/Election Requirement in the U.S. Patent and Trademark Office.
U.S. Appl. No. 13/741,663 dated Mar. 14, 2014, Final Office Action in the U.S. Patent and Trademark Office.
U.S. Appl. No. 13/741,663 dated Jul. 3, 2013, Restriction/Election Requirement in the U.S. Patent and Trademark Office.
U.S. Appl. No. 13/741,663 dated Sep. 3, 2013, Office Action in the U.S. Patent and Trademark Office.
"Coffee, Tea, Mate, Methylxanthines and Methylglyoxal," IARC Monographs on the Evaluation of Carcinogenis Risks to Humans, 1991; 51:60-89.
Barclay et al., "Glucosamine," The Annals of Pharmacotherapy, 1998; 32(5):574-579.
Castelluccio et al., "Antioxidant Potential of Intermediates in Phenylpropanoid Metabolism in Higher Plants," FEBS Letters, 1995; 368:188-192.
Duke et al., CRC Handbook of Medicinal Herbs, pp. 130-132; CRC Press, Inc., Boco Raton, FL., first printed 1985.
English abstract translation for JP 3127973 published May 31, 1991. Inventors: Chizuko et al.
Fuster, M. D., Mitchell, A. E., Ochi, H., Shibamoto, T. Antioxidative Activities of Heterocyclic Compounds Formed in Brewed Coffee. J. Agric. Food Chem, 2000; 48(11):5600-5603.
Guminska et al., "In Vitro Inhibitory Effect of Chitosan and its Degradation Products on Energy Metabolism in Ehrlich Ascites Tumor Cells; (EAT)," Polish Journal of Pharmacology; 1996; 48(5):495-501.

(56) References Cited

OTHER PUBLICATIONS

Hartman et al., "Tea and Coffee Consumption and Risk of Colon and Rectal Cancer in Middle-Aged Finnish Men," Nutrition and Cancer, 1998; 31(1):41-48.

Huang et al., "Inhibitory Effect Of Curcumin, Chlorogenic Acid, Caffeic Acid, and Ferulic Acid on Tumor Promotion in Mouse Skin by 12-0-Tetradecanoylphorbol-13-acetate," Cancer Research, 1988; 48:5941-5946.

Johnson et al., "Genetic Analysis of Life-Span in *Caenorhabditis elegans*," Proc. Natl. Acad. Sci. USA, 1982; 79:6603-6607.

Karim et al.; "Effects of Cocoa Extracts on Endothelium-Dependent Relaxation[1]"; Journal of Nutrition (supplement to) American Society for Nutritional Sciences, 2000; 2105S-2108S.

Kimura et al., "Prevention of Chitosan of Myelotoxicity, Gastrointestinal Toxicity and Immunocompetent Organic Toxicity Induced by 5-Fluorouracil without Loss of Antitumor Activity in Mice," Jpn J. Con. Res., 1999; 90:765-774.

Maskaleris et al., "Induction of Ofcytogenetic Damage in Human Lymphocytes In Vitro and of Antineoplastic Effects in Ehrlich Ascites Tumor Cells In Vivo Treated by Methotrexate, Hyperthermia and/or Caffeine," Mutation Research, 1998; 422(2):229-236.

Nepka et al., "Chemopreventive Activity of Very Low Dose Dietary Tannic Acid Administration in Hepatoma Beating C3H Male Mice," Cancer Letters, 1999; 141(1):57-62.

Olthof et al, "Chlorogenic Acid and Caffeic Acid are Absorbed in Humans," The Journal of Nutrition, 2001; 131(1):66-71.

Pittler et al., "Randomized, double-blind trial of chitosan for body weight reduction," European Journal of Clinical Nutrition, 1999; 53:379-381.

Shimizu et al., "Suppressive Effects of Chlorogenic Acid on N-Methyl-N-Nitrosourea-Induced Glandular Stomach Carcinogenesis in Male F344 Rats," The Journal of Toxicological Sciences, 1999; 24(5):433-439.

Szekely, T., "Caffeine as a Stimulant Against Suicide," Arch. Intern Med., 1997; 157(2):243-244.

Takahashi, et al.; "Combined Effect of CDDP and Caffeine Against Human Gastric Cell Line in Vivo"; Anticancer Research; 1998; vol. 18: pp. 4399-4401.

Tanaka et al, "Inhibition of 4-Nitroquinoline-1-oxide-induced Rat Tongue Carcinogenesis by the Naturally Occurring Plant Phenolics Caffeic, Ellagic, Chlorogenic and Ferulic Acids," Carcinogenesis, 1993; 14(7):1321-1325.

Torzsas et al., "The Influence of High and Low Molecular Weight Chitosan on Colonic Cell Proliferation and Abberant Crypt Foci Development in CF1 Mice," Food and Chemical Toxicology, 1996; 34(1):73-77.

Vinson et al.; "Vitamins and Especially Flavonoids in Common Beverages Are Powerful in vitro Antioxidants which Enrich Lower Density Lipoteins and Increase Their Oxidative Resistance after Ex Vivo Spiking in Human Plasma"; J. Agric. Food Chem.,1999; 47(7):2502-2504.

\* cited by examiner

METHOD FOR ENHANCING POSTPROCESSING CONTENT OF BENEFICIAL COMPOUNDS IN BEVERAGES NATURALLY CONTAINING SAME

CITATION TO PARENT APPLICATION(S)

This application is a continuation of U.S. application Ser. No. 13/741,663, filed Jan. 15, 2013, now abandoned, which is a continuation of U.S. application Ser. No. 12/749,163, filed Mar. 29, 2010, which now U.S. Pat. No. 8,357,419, which is a continuation of U.S. application Ser. No. 10/962,758, filed Oct. 12, 2004, now U.S. Pat. No. 7,713,566, which in turn is a continuation-in-part of U.S. application Ser. No. 10/493,780now abandoned, which was filed Apr. 26, 2004, as the National Stage Application of PCT/US02/35053. PCT/US02/35053, filed Oct. 31, 2002 claims priority to U.S. application, Ser. No. 10/001,928, filed Oct. 31, 2001, now U.S. Pat. No. 6,723,368, issued Apr. 20, 2004, which was a continuation-in-part with respect to U.S. application, Ser. No. 09/843,543, filed Apr. 25, 2001, now abandoned which was a continuation-in-part of U.S. application Ser. No. 09/481,279, filed Jan. 11, 2000, now U.S. Pat. No. 6,669,979 which, in turn, was a continuation-in-part of U.S. application Ser. No. 09/468,560, filed on Dec. 21, 1999, now abandoned from all of which priority is claimed under 35 U.S.C. § 120.

BACKGROUND OF THE INVENTION

1. Field of the Invention

The present invention relates to conventional foods, beverages, and nutritional supplements.

2. Background Information

Recent research indicates that polyphenols in fruits, vegetables, common beverages and plants possess the capacity for diversified, beneficial pharmacological activities. It is widely accepted that these compounds, recently dubbed "vitamin P", possess a wide range of beneficial pharmacological activities which include stabilizing capillary wall tissues, quenching free radicals, maintaining proper permeability and flexibility of capillaries, and preventing cardiovascular diseases. (C. Castelluccio, et. al. FEBS Letters 368 (1995) 188-192). Numerous studies have also shown that most plant polyphenols possess cancer preventive capacity because of their profound antioxidant activity.

It is, of course, well-known that coffee contains caffeine. However, a lesser-known fact is that coffee contains potentially highly beneficial condensed tannin and polyphenolic acids.

Phenolic acids in coffee are mainly esters of quinic acid with different amount of caffeyl groups attached to its different positions. The phenolic acids present in coffee such as chlorogenic acid, caffeic acid, and para-coumaric acid have been shown to exert cancer preventive activities in animal models. Chlorogenic acid has also been found to inhibit methylazoxymethanol-induced large intestinal tumors in hamster.

Chlorogenic acid, which is the main phenolic acid in coffee, is able to protect the gastric mucosa against irritations, and, therefore, improves the digestibility of foods, beverages and medicaments. The improved digestibility is expressed through a much-reduced systemic acid secretion (such as causes heartburn, etc.), which has been found to be directly dependent on an increased level of chlorogenic acid content in raw green coffee beans.

Normally the natural chlorogenic acid content of green coffee is reduced by approximately 40 to 80% during conventional roasting process. Analysis by the present inventor indicates that green coffee beans which initially contain 8% phenolic acids contain, respectively, 2% phenolic acids when light roasted, 1% when medium roasted, and less than 0.5% when dark roasted. This clearly represents a significant loss of beneficial compounds. Thus, the use of a roasting process which is designed to preserve the polyphenols normally lost through the roasting process will result in a product which has concentrations of phenolic compounds in greater quantities than currently marketed coffee beverages.

The resulting beverage will also be a source of diterpenes which have detoxification properties in humans, as well as other beneficial compounds such as triterpenes.

Furthermore, along with the potential health benefits achieved in the beverage substrate with the said process, antioxidants also have the ability to increase the duration and freshness of conventional foods and beverages. This fact has been known and practiced for many decades in the food industry. Antioxidants reduce the oxidation potential of the constituents found in plant derived foods and beverages which can provide an extended shelf life and stability of the final product.

DETAILED DESCRIPTION OF THE PREFERRED EMBODIMENT

Extensive research by the present inventors produced a finding that post-processing chlorogenic acid content in particular, and total polyphenol content in general, can be substantially enhanced for brewed coffee through a remarkably simple process. The same is true of other brewed beverages the counterpart substrates of which are known to have a significant polyphenolic constituent. Therefore, while the predominant discussion in this specification focuses on coffee, it must be understood that similar results can be obtained through practice of the methods of the present invention in the context of producing beverages from other materials which naturally contain polyphenolic acids (teas, for example).

The present inventors have discovered that, if applied in the manner prescribed herein, the remarkably simple process of soaking coffee beans in plain water prior to roasting, and, after roasting, "quenching" the beans with a portion of the pre-soak liquid (the soaking water, plus the polyphenols released into the water) will substantially enhance the post-roasting polyphenol content of coffee beans. This represents yet another significant leap forward in the present inventors' work in optimizing the post-processing polyphenol content of coffee as a means for delivering health-enhancing agents to consumers in a most non-intrusive and cost effective manner.

The process of the present invention, when compared with earlier, related processes developed by the present inventors, not only provides a substantial health benefits potential, but permits such benefits to be realized, and the product which carries the benefits to be distributed and sold, with no market or distribution related impediments or inconveniences. This is true, in part, because, unlike some of the referenced prior processes (the subject of first parent application relating to this continuation application) the process for spiking polyphenolics pursuant to the present invention, at least in the case of coffee, takes place at the commercial, roasting stage, rather than at the retail sales level and is, therefore, completely transparent to the end consumer.

Illustrative examples of processes of the present invention follow. It should be understood, of course, that commercial processing according to the present invention will take place on much larger scales than the illustrative examples provided, with proportional increases in the respective constituents (coffee beans, water, pre-soak liquid used for quenching, etc) for larger batches. The first described example is presently believed to be the optimal process for maximizing polyphenol content in coffee beans and ultimately, therefore, in brewed coffee.

According to the most economical version of the present invention, raw, green coffee beans are "pre-soaked" in water as described in more detail hereafter, and a portion (approximately 10% to 20%) of the same water is later used to quench the same beans immediately after roasting. However, as shown below, variations of the same invention involve pre-soaking green coffee beans, roasting other beans, and quenching the roasted beans with the solution from soaking the first, non-roasted beans. These later methods yield end products of even greater phenolics content.

The level of polyphenols, such as chlorogenic acid, in the presoak liquid depends on the variation in the water temperature of soak and the length or duration of the soak. It will typically range from 15%-30% with the optimum level achieved between 25%-28% total chlorogenic acid. Additionally, an increase in the level of polyp he no ls in the presoak liquid quite possibility could be achieved by concentrating the presoak liquid after filtration from the beans. This result was achieved in the lab through sonication and could be achieved in the production process through familiar unit operations such as evaporation. An increase in the concentration of polyphenols in the presoak liquid could have a significant impact on the level of polyphenols achieved after quenching.

EXAMPLE 1

Raw green coffee beans are pre-soaked in water for 3 hours at 75 deg C. 1000 grams of green beans soaked in 2000 mls of water. 1000 mls of pre-soak solution (water used for pre-soaking) was retained after beans are removed from water for roasting. 650 grams of pre-soaked green beans are roasted in a traditional coffee roaster with temperature starting at 350 deg F. and increasing to 430 deg F. over a period of approximately 15-18 minutes.

At the conclusion of the roast, the beans are dropped into a container and immediately quenched with 150 mls of the pre-soak solution that contains 23% total chlorogenic acid. The container is agitated slightly to evenly distribute the presoak liquid onto the roasted beans and ensure uptake of the liquid into the bean cell wall. It should be noted the quench step does not produce a roasted bean that is saturated only slightly coated with the presoak liquid. The roasted beans are air-dried and the roasted beans are then ground to a powder and brewed with hot water to produce a coffee beverage.

Chemical analysis showed that the new beverage contains over 20%-65% of the pre-roasted phenolic acid content, specifically representing chlorogenic acid content at 40% 150% (depending on degree of roast—bigger increase with darker roast) over that in traditional roasted coffee of a similar roast color.

EXAMPLE 2

Raw green coffee beans are pre-soaked in water for 3 hours at 80 deg C. 1000 grams of green beans soaked in 2000 mls of water. During the presoak step the beans are completely submersed in water and the soak tank is slightly agitated. 1000 mls of pre-soak solution was obtained Pre-soak water with a chlorogenic acid content of 25% is collected for later quenching step. 1400 grams of regular green beans are roasted in a traditional manner. Upon completion of the roast while the beans are still very hot (>400 deg F.) the beans are split into a control and an experimental group and subsequently quenched with either 150 mls of water (control) or 150 mls of the pre-soak solution that has been previously collected from green beans. Quenching consists of atomizing the presoak liquid onto the bean in an even dispersed manner to achieve a bean contact surface area of >90%. (experimental). The green beans used to create the pre-soak quenching solution are not the beans that are use in the roasting. The roasted beans are air-dried then ground to a powder and brewed with hot water to produce a coffee beverage.

Chemical analysis showed that the new beverage contains over 20%-70% of phenolic acid content, representing a 40% -200% chlorogenic acid content over that of the control of the same roast.

EXAMPLE 3

Raw green coffee beans are pre-soaked in water for 3 hours at 80 deg C. 1000 grams of green beans soaked in 2000 mls. of water. 1000 mls of pre-soak solution was obtained. Pre-soak water is collected for later quenching step. A portion of the pre-soak water is collected and freeze dried to be used as a fortifying ingredient in the pre-soak quench. 1400 grams of regular green beans are roasted in a traditional manner. Upon completion of the roast the beans are split into a control and an experimental group and subsequently quenched with either 150 mls of water (control) or 150 mls of the pre-soak which has been fortified with 10 grams of freeze dried pre-soak. All pre-soak solution has been previously collected and/or collected and freeze dried from green beans. (experimental). The green beans used to create the pre-soak quenching solution are not the beans that are use in the roasting. The roasted beans are then air dried, ground to a powder and brewed with hot water to produce a coffee beverage.

Chemical analysis showed that the new beverage contains over 120% of phenolic acids, representing approx 250% of chlorogenic acid content of conventionally processed coffee.

EXAMPLE 4

Raw green coffee beans are pre-soaked in water for 4 hours at 80 deg C. 1000 grams of green beans soaked in 2000 mls of water. The presoak liquid was decanted and separated from the beans. A vacuum of −20 inches Hg was applied to the soaked beans to remove any additional high polyphenol liquid engaged onto the bean. 100 mls of pre-soak liquid along with an additional 100 mls of vacuum filtrate were collected and used as the quench water. The total chlorogenic acid content of the quench liquid was 28%. 1400 grams of regular green beans are roasted in a traditional manner. Upon completion of the roast while the beans are still very hot (>400 deg F.) the beans are split into a control and an experimental group and subsequently quenched with either 150 mls of water (control) or 150 mls of the pre-soak solution that has been previously collected from green beans. Quenching consists of atomizing the presoak liquid onto the bean in an even dispersed manner to achieve a bean contact surface area of >90%. The green beans used to create the pre-soak quenching solution are not the beans that are use in the roasting. The roasted beans are air-dried then ground to a powder and brewed with hot water to produce a coffee beverage.

Chemical analysis showed that the new beverage contains over 80% of phenolic acid content, representing a 200% chlorogenic acid content over that of the control of the same roast.

Studies completed by a team of scientists at the University of California, Davis lead by Shibamoto (Shibamoto, et. al., J. Agric. Food Chem., Vol 48, No. 11, 2000) indicate there are a number of volatile chemicals, specifically Heterocyclic compounds formed during conventional brewing processes. These compounds including thiophenes, thiazoles, pyrroles, pyrazines and furans, to name a few, have demonstrated some medicinal activities as well. Therefore it may be possible during the quench step of the process to reclaim these theoretically potent constituents with slight modifications in process equipment.

EXAMPLE 5

Raw green coffee beans are pre-soaked in water for 3 hours at 80 deg C. 1000 grams of green beans soaked in 2000 mls of water. The presoak liquid was decanted and separated from the beans. 1000 mls of Pre-soak liquid was collected and used as the quench water. The total chlorogenic acid content of the quench liquid was 24%. 1400 grams of regular green beans are roasted in a traditional manner. Upon completion of the roast while the beans are still very hot (>400 deg F.) the beans are split into a control and an experimental group and subsequently quenched with either 150 mls of water (control) or 150 mls of the pre-soak solution that has been previously collected from green beans. In this example quenching consists of atomizing the presoak liquid onto the bean in an even dispersed manner to achieve a bean contact surface area of >90% in an enclosed fluid bed where no steam is allowed to escape throughout the quenching and drying process. The vent vapors are condensed in a reflux chamber and reintroduced back into the fluid bed. The green beans used to create the pre-soak quenching solution are not the beans that are use in the roasting. When the roasted beans are fully air-dried and cooled they are ground to a powder and brewed with hot water to produce a coffee beverage.

HPLC analysis showed that the new beverage contains over 80% of phenolic acid content, representing a 200% chlorogenic acid content over that of the control of the same roast. Further analysis from UV absorbance indicated a presence of additional antioxidant compounds that may have been captured from the volatile vapors further research needs to be conducted to characterize these compounds and determine their antioxidant activities.

The powder from the preceding examples can be sold as coffee powder for brewing, instant coffee, or can be brewed and sold as a ready-to-drink coffee beverage. The resulting product can be taken as a food or functional food by a human or other mammal, orally.

EXAMPLE 6

Raw green coffee beans are pre-soaked in water for 4 hours at 95 deg C. 34 kilograms of green beans soaked in 72 liters of water. Drain off the presoak liquid. While the presoak liquid is still hot, add to the presoak liquid 2.55 kilograms of green coffee bean extract purified to greater than 60% total polyphenolic acids, or other water soluble antioxidant based extract with a similar concentration. Allow mixture to agitate for 30 minutes at 60 deg. C. This presoak liquid will now be a concentrated polyphenol solution containing greater than 8% polyphenols.

Roast 250 kilograms of beans at conventional roasting conditions (450 deg F., 7 minutes or roast to achieve desired bean sensory profile). Once roast is complete, quench beans with 32 liters of concentrated presoak liquid for 50 seconds. Allow beans to cool and package accordingly. Note: by discharging the roasted beans immediately after roasting, while still hot, into an appropriate mixer—an example might include a fluidized bed mixer such as a Forberg as commonly known in the field—optimum quench or distribution of the presoak liquid onto the beans can be achieved before the beans are allowed to cool. The optimum temperature for concentrated polyphenol liquid absorption into the bean cell wall is at a bean temperature of greater than 375 deg F. Beans can be ground or packaged as whole beans. It may be necessary, once beans are cool, to slightly agitate them to obtain a free flowing product. The final brewed coffee polyphenol content is 160 mg. per serving.

CONCLUSIONS

The preceding examples illustrate that a more healthful polyphenol coffee beverage product can be produced by a very simple variation of conventional coffee roasting methods. In addition, an end product which is healthier and not much more costly than existing coffee powders can be produced, and thereby provide a market and economic benefit to vendors. The present method yields a product which is in no way undesirable from an aesthetic standpoint (taste, aroma, etc. is unaffected). Thus, there is no reason not to, and every reason to, adopt the present coffee roasting processing methods for the well being of consumers.

The potential to increase the antioxidant capacity in the beverage substrate, in this case roasted coffee, provides an end product that has increased stability through a reduction in oxidation potential. Reducing the oxidizing potential of the beverage substrate allows a product to maintain its freshness, taste profile, and other product characteristics for a longer duration than would be achieved through conventional processing methods.

The processes of the present invention represent significant departures from conventional production of roasted coffee products, where green beans are simply roasted and mayor may not be quenched with water, whereas the end product of the present invention achieves a chemical profile of increased amounts of phenolic acids and other beneficial compounds which is different from existing roasted coffee brews. This new process yields more active, more bioavailable, and larger quantities of phenolic compounds than those found in existing roasted coffee brews.

Although the invention has been described with reference to specific embodiments, this description is not meant to be construed in a limited sense. Various modifications of the disclosed embodiments, as well as alternative embodiments of the inventions will become apparent to persons skilled in the art upon the reference to the description of the invention. It is, therefore, contemplated that the appended claims will cover such modifications that fall within the scope of the invention.

What is claimed is:

1. A method of producing a beverage substrate, the method comprising the steps of:
   selecting a measure of beverage substrate, wherein the beverage substrate comprises polyphenolic acids;
   immersing said beverage substrate in pre-soak liquid containing water;

removing said beverage substrate from said pre-soak liquid, collecting a portion of said liquid creating a post-immersion liquid and drying the portion of said pre-soak liquid, and roasting said beverage substrate; and quenching said beverage substrate after said roasting with a portion of said post-immersion pre-soak liquid.

2. The method of claim 1 wherein the quenching further includes a water soluble antioxidant-based extract.

3. The method of claim 1 wherein said beverage substrate is coffee beans.

4. A method of producing a beverage substrate, the comprising the steps of:

selecting a first measure of beverage substrate, wherein the beverage substrate comprises polyphenolic acids;

immersing said first measure of beverage substrate in a pre-soak liquid containing water;

collecting said pre-soak liquid after said immersing, collecting a portion of said liquid creating a post-immersion liquid and drying the portion of said pre-soak liquid, roasting a second measure of beverage substrate; and quenching said second measure of beverage substrate after said roasting with a portion of said post-immersion liquid.

5. The method of claim 4 wherein the quenching further includes a water soluble antioxidant-based extract.

6. The method of claim 4 where said first measure of beverage substrate comprises coffee beans.

7. The method of claim 4 wherein said second measure of beverage substrate comprises coffee beans.

8. The method of claim 4 wherein said first measure of beverage substrate and said second measure of beverage substrate comprises coffee beans.

9. A method of producing a beverage substrate, the method comprising the steps of:

selecting a first measure of beverage substrate, wherein the beverage substrate comprises polyphenolic acids;

immersing said first measure of beverage substrate in a pre-soak liquid containing water;

collecting the pre-soak liquid after said immersing, creating a post-immersion pre-soak liquid;

drying the portion of the pre-soak liquid;

roasting a second measure of beverage substrate; and quenching the second measure of beverage substrate after the roasting with a solution comprising the dried post-immersion pre-soak liquid.

10. The method of claim 9 where said first measure of beverage substrate comprises coffee beans.

11. The method of claim 9 wherein said second measure of beverage substrate comprises coffee beans.

12. The method of claim 9 wherein said first measure of beverage substrate and said second measure of beverage substrate comprises coffee beans.

13. The method of claim 9 where the quenching further includes a water soluble antioxidant-based extract.

* * * * *